United States Patent
Gast et al.

(12) 
(10) Patent No.: US 6,326,392 B1
(45) Date of Patent: Dec. 4, 2001

(54) ANTI-ESTROGEN PLUS PROGESTIN CONTAINING ORAL CONTRACEPTIVES

(75) Inventors: Michael J. Gast, Phoenixville; Christopher P. Miller, Wayne, both of PA (US)

(73) Assignee: American Home Products Corporation, Madison, NJ (US)

(*) Notice: Subject to any disclaimer, the term of this patent is extended or adjusted under 35 U.S.C. 154(b) by 0 days.

(21) Appl. No.: 09/185,058

(22) Filed: Nov. 3, 1998

Related U.S. Application Data

(60) Provisional application No. 60/093,051, filed on Nov. 6, 1997.

(51) Int. Cl.[7] .......................... A61K 31/405; A61K 31/56
(52) U.S. Cl. .............................................. 514/415; 514/171
(58) Field of Search ....................................... 514/415, 171

(56) References Cited

U.S. PATENT DOCUMENTS

| | | | |
|---|---|---|---|
| 4,943,572 | 7/1990 | von Angerer | 514/235.2 |
| 5,023,254 | 6/1991 | von Angerer | 514/235.5 |
| 5,124,335 | 6/1992 | Patchett et al. | 514/300 |
| 5,496,844 | 3/1996 | Inai et al. | 514/415 |
| 5,550,107 | 8/1996 | Labrie | 514/11 |
| 5,591,753 | 1/1997 | Black et al. | 514/324 |
| 5,646,137 | 7/1997 | Black et al. | 514/171 |
| 5,672,609 | 9/1997 | Bryant et al. | 514/318 |
| 5,998,402 | * 12/1999 | Miller et al. | 514/212 |

FOREIGN PATENT DOCUMENTS

| | | |
|---|---|---|
| 2208321 | 7/1996 | (CA) . |
| 0639567 | 2/1995 | (EP) . |
| 0791356 | 8/1997 | (EP) . |
| 0792641 | 9/1997 | (EP) . |
| 1326528 | 8/1973 | (GB) . |
| 9310741 | 6/1993 | (WO) . |
| 9426105 | 11/1994 | (WO) . |
| 9517383 | 6/1995 | (WO) . |
| 9603375 | 2/1996 | (WO) . |

OTHER PUBLICATIONS von Angerer et al., Amer. Chem. Soc., pp. 2635–2640, 1990.
von Angerer et al., Amer. Chem. Soc., pp. 132–136, 1986.
Biberger et al., J. Steroid Biochem. Molec. Biol., vol. 58, No. 1, pp. 31–43, 1996.
Henderson et al., Ann. N.Y. Aca. Sci., pp. 176, 177, 189, 1995.
Oparil "Hypertension in postmenopausal Woman:Pathology and Management" EMBASE 95:283951, 1995.
von Angerer et al., J. Med. Chem. vol. 27, pp. 1439–1447, 1984.

* cited by examiner

*Primary Examiner*—Theodore J. Criares
*Assistant Examiner*—Jennifer Kim
(74) *Attorney, Agent, or Firm*—Arnold S. Milowsky

(57) ABSTRACT

This invention provides a method of providing contraception which comprises administering to a female of child bearing age a combination of a non-uterotrophic anti-estrogen and a progestin for 28 days per 28-day menstrual cycle.

13 Claims, No Drawings

ANTI-ESTROGEN PLUS PROGESTIN CONTAINING ORAL CONTRACEPTIVES

This application claims the benefit of U.S. Provisional Application No. 60/093,051, which was converted from U.S. patent application Ser. No. 08/965,083, filed Nov. 6, 1997, pursuant to a petition filed under 37 C.F.R. 1.53(c)(2)(i) on Apr. 15, 1998.

BACKGROUND OF THE INVENTION

This invention relates to oral contraceptive regimens containing a non-uterotrophic antiestrogen (i.e., a tissue selective estrogen) and a progestin.

The vast majority of oral contraceptives consist of a combination of a progestin and estrogen that are administered concurrently for 21 days followed either by a 7 day pill free interval or by the administration of a placebo for 7 days in each 28 day cycle. The most important aspects of a successful oral contraceptive product are effective contraception, good cycle control (absence of spotting and breakthrough bleeding and occurrence of withdrawal bleeding), and minimal side effects. Combination oral contraceptives have traditionally acted by suppression of gonadotropins. In addition, it appears that the progestin component is primarily responsible for contraceptive efficacy through inhibition of ovulation, and other peripheral effects which include changes in the cervical mucus (which increase the difficulty of sperm entry into the uterus) and the endometrium (which reduce the likelihood of implantation). The estrogenic component intensifies the anovulatory effect of the progestin, and is also important for maintaining cycle control.

Several examples of progestin only contraceptives are known. For example products containing norethindrone (350 µg) or levonorgestrel (75 µg) are available, but raise several issues which limit their ultimate acceptability. The first is that currently available oral progestin only contraceptives are administered at doses that fail to completely inhibit ovulation thus pregnancy rates are marginally higher than currently available combined oral contraceptive preparations. Nonetheless, the pregnancy rates (generally less than 3 per 100 women per year) are excellent and are based primarily on cervical mucous changes and modest changes in endometrium. The second difficulty with these preparations is the extraordinarily high rate of abnormal or unexpected vaginal bleeding in women who utilize them. The absence of predictable vaginal bleeding which results from irregular development and shedding of the uterine lining (endometrium) is a phenomenon that is common to injectable, implantable and oral progestin only contraceptives. This side-effect is reported by up to 80% of women using any of these forms of progestin only contraception.

GB Patent Specification 1326528 discloses estrogen antogonizing agents (preferrably cis-clomiphene) in combination with a progestin for use as a contraceptive. The estrogen antagonists disclosed in GB 1326528 are uterotrophic (see Kumar, A. India. J. Biosc. 20(5): 665 (1995)) whereas the anti-estrogens of this invention are not.

DESCRIPTION OF THE INVENTION

This invention provides a contraceptive regimen for females of child-bearing age which comprises administering a combination of a non-uterotrophic anti-estrogen and a progestin continuously during the 28-day menstrual cycle. Non-uterotrophic antiestrogens are defined as those which typically will not produce clinically significant endometrial proliferation. More particularly, this invention provides a method providing contraception to a female of child bearing age which comprises administering a contraceptive effective amount of a combination of a non-uterotrophic anti-estrtogen of formulas I or II having the structures

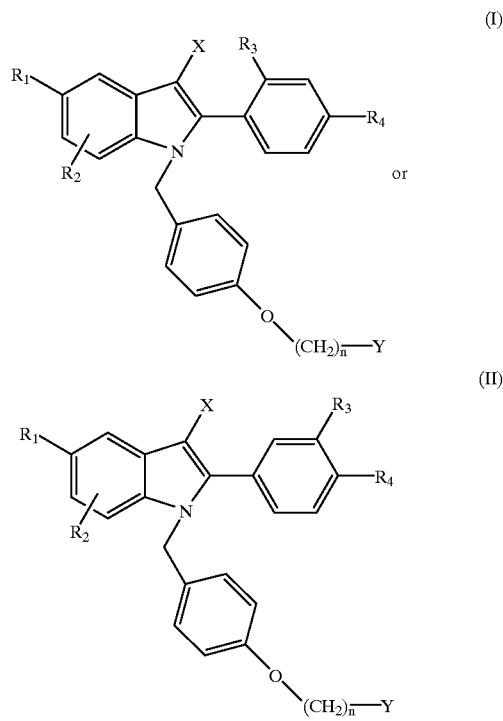

wherein:
R$_1$ is H, OH, carboalkoxy of 2–12 carbon atoms, alkoxy of 1–12 carbon atoms, halogen or mono- or poly-fluoroalkoxy of 1–12 carbon atoms;

R$_2$ is H, OH, carboalkoxy of 2–12 carbon atoms, alkoxy of 1–12 carbon atoms, halogen, mono- or poly-fluoroalkoxy of 1–12 carbon atoms, cyano, alkyl fo 1–6 carbon atoms, or trifluoromethyl, with the proviso that, when R$_1$ is H, R$_2$ is not OH.

R$_3$ and R$_4$ are each, independently, H, OH, carboalkoxy of 2–12 carbon atoms, alkoxy of 1–12 carbon atoms, halogen, mono- or poly-fluoroalkoxy of 1–12 carbon atoms, or cyano, with the proviso that, when R$_1$ is H, R$_2$ is not OH.

X is H, alkyl of 1–6 carbon atoms, cyano, nitro, triflouromethyl, or halogen;

n is 2 or 3;

Y is a saturated, partially saturated or unsaturated 5–7 membered heterocycle containing a nitrogen, which may optionally contain a second heteroatom selected from the group consisting of —O—, —NH—, alkylamine of 1–6 carbon atoms, —N═, and S(O)$_m$;

m is 0–2;

or a pharmaceutically acceptable salt thereof, and a progestin for 28 consecutive days per 28-day menstrual cycle.

Preferred compounds are those in which

R$_1$ is selected from H, OH or the C$_1$–C$_{12}$ esters or alkyl ethers thereof, halogen; R$_2$, R$_3$, R$_4$, R$_5$, and R$_6$ are independently selected from H, OH or the C$_1$–C$_{12}$ esters or alkyl ethers thereof, halogen, cyano, C$_1$–C$_6$ alkyl, or trihalomethyl, preferably trifluoromethyl, with the proviso that, when R$_1$ is H, R$_2$ is not OH;

X is selected from H, $C_1$–$C_6$ alkyl, cyano, nitro, triflouromethyl, halogen;

and Y is 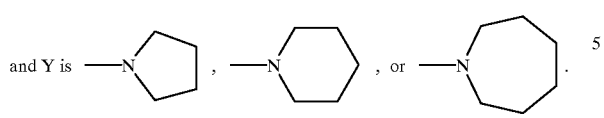

The preparation of the anti-estrogens of Formulas I and II is disclosed in U.S. patent application Ser. No. 08/833,271, filed Apr. 4, 1997, which is hereby incorporated by reference.

Specifically preferred anti-estrogens of formulas I and II are shown in the Tables below.

TABLE 1

| Example No. | X | Q | Z |
|---|---|---|---|
| No. 1 | OBn | 4'-OEt |  |
| No. 2 | OBn | H |  |
| No. 3 | OBn | 4'-OBn |  |
| No. 4 | OBn | 4'-OBn |  |
| No. 5 | OBn | 4'-F |  |
| No. 6 | OBn | 4'-F |  |

TABLE 1-continued

| Example No. | X | Q | Z |
|---|---|---|---|
| No. 7 | OBn | 4'-Cl |  |
| No. 8 | OBn | 3',4'-OCH$_2$O— |  |
| No. 9 | OBn | 4'-O-iPr |  |
| No. 10 | OBn | 4'-CH$_3$ |  |
| No. 11 | OBn | 3'-OBn |  |
| No. 12 | OBn | 3'-OBn |  |
| No. 13 | OBn | 4'-OBn,3'-F |  |
| No. 14 | OBn | 4'-OBn,3'-F |  |
| No. 15 | OBn | 3'-OMe |  |

TABLE 1-continued
| Example No. | X | Q | Z |
|---|---|---|---|
| No. 16 | OBn | 4'-OCF$_3$ | 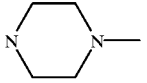 |
| No. 17 | OBn | 4'-OBn |  |
| No. 18 | OBn | 3'-OMe |  |
TABLE 2
| Example No. | X | Q | Z |
|---|---|---|---|
| No. 19 | H | H |  |
| No. 20 | H | 4'-OH |  |
| No. 21 | OH | H |  |
| No. 22 | OMe | 4'-OH |  |
| No. 23 | OH | 4'-OMe |  |
| No. 24 | OMe | 4'-OMe | |
| No. 25 | OMe | 4'-OMe |  |
| No. 26 | OH | 4'-OEt | |
| No. 27 | OH | 4'-OEt |  |
| No. 28 | F | 4'-OH |  |

TABLE 2-continued

| Example No. | X | Q | Z |
|---|---|---|---|
| No. 29 | OH | H | azepane (7-membered N ring) |
| No. 30 | OH | 4'-OH | pyrrolidine |
| No. 31 | OH | 4'-OH | piperidine |
| No. 32 | OH | 4'-OH | azepane |
| No. 33 | OH | 4'-OH | azocane (8-membered N ring) |
| No. 34 | OH | 4'-F | piperidine |
| No. 35 | OH | 4'-F | azepane |
| No. 36 | OH | 3'-OMe,4'-OH | piperidine |
| No. 37 | OH | 3',4'-OCH$_2$O— | piperidine |
| No. 38 | OH | 4'-O-iPr | piperidine |
| No. 39 | OH | 4'-O-iPr | azepane |
| No. 40 | OH | 4'-O-Cp | piperidine |

TABLE 2-continued
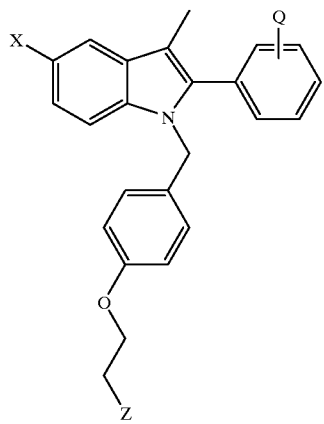
| Example No. | X | Q | Z |
|---|---|---|---|
| No. 41 | OH | 4'-Cl | 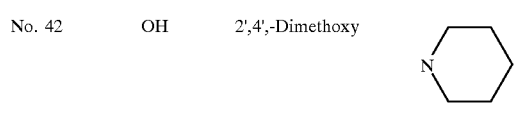 |
| No. 42 | OH | 2',4',-Dimethoxy | 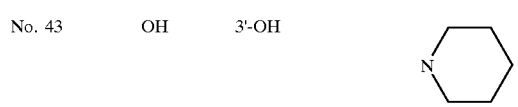 |
| No. 43 | OH | 3'-OH | 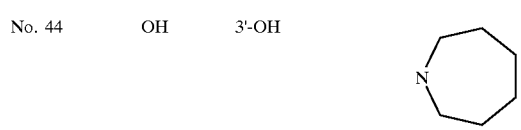 |
| No. 44 | OH | 3'-OH | 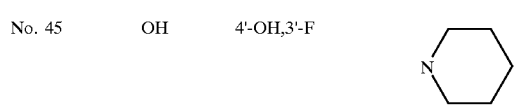 |
| No. 45 | OH | 4'-OH,3'-F | 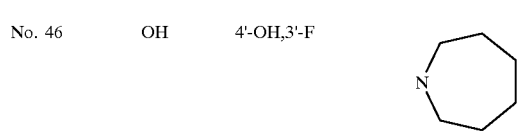 |
| No. 46 | OH | 4'-OH,3'-F | |
TABLE 2-continued
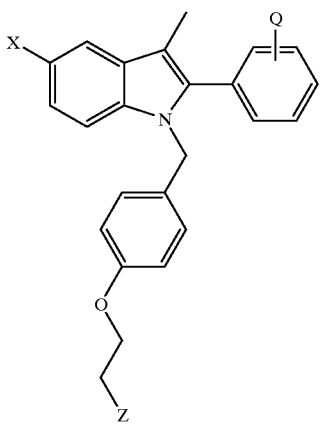
| Example No. | X | Q | Z |
|---|---|---|---|
| No. 47 | OH | 3'-OMe | |
| No. 48 | OH | 4'-OCF$_3$ | |
TABLE 3
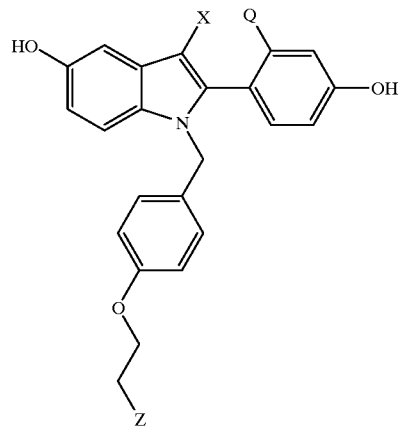
| Example No. | X | Q | Z |
|---|---|---|---|
| No. 49 | Cl | H |  |

TABLE 3-continued

[Structure: indole with HO- at 5-position, X at 3-position, 2-(Q-substituted-4-hydroxyphenyl) at 2-position, and N-benzyl with 4-(2-Z-ethoxy) substituent]

| Example No. | X | Q | Z |
|---|---|---|---|
| No. 50 | Cl | H | piperidinyl |
| No. 51 | Cl | H | azepanyl (7-membered N ring) |
| No. 52 | Cl | CH₃ | piperidinyl |
| No. 53 | Et | H | piperidinyl |
| No. 54 | CN | H | piperidinyl |
| No. 55 | CN | H | azepanyl |

TABLE 4

[Structure: indole with RC(O)O- at 5-position, 3-methyl, 2-(4-RC(O)O-phenyl), N-benzyl with 4-(2-Z-ethoxy) substituent]

| Example No. | R | Z |
|---|---|---|
| No. 56 | Et | azepanyl |
| No. 57 | t-Bu | azepanyl |
| No. 58 | t-Bu | piperidinyl |

Particularly preferred anti-estrogens of Formulas I or II are those of Examples 31 and 32 in the tables above. It is preferred that the anti-estrogen of Formulas I or II is administered at a daily dosage equivalent to 0.1–150 mg of the compound of Example 32.

Preferred progestins include, but are not limited to levonorgestrel, norgestrel, desogestrel, 3-ketodesogestrel, norethindrone, gestodene, norethisterone acetate, norgestimate, osaterone, cyproterone acetate, trimegestone, dienogest, and drospirenone. It is more preferred that the progestin is levonorgestrel. When levonorgestrel is used as the progestin, it is preferred that the daily dosage of levonorgestrel is 30–150 μg, with 50–110 μg being more preferred, and 75–100 μg being most preferred. The following table shows the preferred dosages of representative progestins of this invention.

PREFERRED PROGESTIN DAILY DOSAGE RANGES

| Progestin | Dosage |
|---|---|
| Levonorgestrel | 30–150 μg |
| Norgestrel | 60–300 μg |
| Desogestrel | 45–225 μg |
| 3-Ketodesogestrel | 45–225 μg |
| Norethindrone | 100 μg–1 mg |
| Norethisterone Acetate | 100 μg–1 mg |
| Gestodene | 20–115 μg |
| Norgestimate | 75–500 μg |
| Osaterone | 100 μg–2.5 mg |

-continued

PREFERRED PROGESTIN DAILY DOSAGE RANGES

| Progestin | Dosage |
| --- | --- |
| Trimegestone | 30–1500 µg |
| Dienogest | 500 µg–3.75 mg |
| Drospirenone | 500 µg–3.75 mg |
| Cyproterone Acetate | 450 µg–2.5 mg |

This invention also covers the administration of a combination of other non-uterotrophic anti-estrogens (and preferred daily dosages), such as raloxifene (1–600 mg), droloxifene (1–600 mg), idoxifine (1–600 mg), nafoxidine (0.5–600 mg), toremifene, TAT-59 (0.1–600 mg), levomeloxifene (0.5–600 mg), LY-353381 (1–600 mg), CP-336156, MDL-103323, EM-800, and ICI-182,780 (0.1–150 mg) with a progestin for 28 consecutive days per 28 day menstrual cycle to provide contraception.

This invention also covers other progestins and non-uterotrophic antiestrogens, which will be apparent to one skilled in the art.

It is preferred that the the anti-estrogen plus progestin regimen be administered according to a monophasic type regimen continuously during the 28-day menstrual cycle. In a monophasic regimen, the same dose of each of the anti-estrogen and progestin are administered each day during the administration period. The continuous 28-day administration of the anti-estrogen plus progestin combination will eliminate the withdrawal bleed that is associated with other non-continuous oral contraceptive regimens, and will eliminate the irregular bleeding (breakthrough and spotting) that is associated with progestin only oral contraceptive regimens.

When the compound of Example 32 and levonorgestrel are administered according to a 28-day monophasic regimen, the following dosages are preferred, with regimen A being most preferred.

| Regimen | Example 32 | Levonorgestrel |
| --- | --- | --- |
| A | 2 mg | 90 µg |
| B | 3 mg | 75 µg |
| C | 5 mg | 100 µg |

The anti-estrogen plus progestin contraceptives of this invention can also be administered for 28 days each menstrual cycle according to phased regimens (i.e., biphasic, triphasic, quadraphasic, and the like). In such regimen, the same dosage of the combination is administered each day of the particular phase, with each phase having a different dosage than the preceding or subsequent phase. In a typical quadraphasic regimen, each phase may be 7 days in length. The regimens may be quadraphasic rising regimens in which the dosage of antiestrogen and progestin is increased from phase I to phase II and from phase II to phase III; the dosage during the fourth phase is then typically lower than in the first phase. One skilled in the art will appreciate that this invention also covers regimens in which the dosages of the first or second phase will be highest. Other variations include maintaining a constant dosage of progestin during all four phases, while varying the dosage of antiestrogen of the four phases, with the phase III dosage typically being the highest, and phase IV dosage being the lowest. Alternatively, the dosage of antiestrogen can be held constant during all four phases, while the dosage of progestin is being varied from phase to phase.

For administration, it is preferred that the combination anti-estrogen plus progestin contraceptive be administered in unit dosage form i.e., tablet or pill, with each unit providing the entire daily dosage. It is preferred that the progestin and anti-estrogen are admixed together in the same dosage unit. Such dosage units can be prepared by conventional methodology that is well known to one skilled in the art. In each dosage unit, the contraceptively active progestin and estrogen are combined with excipients, vehicles, pharmaceutically acceptable carriers, and colorants.

This invention also provides a contraceptive kit adapted for daily oral administration which comprises a total of 28 separate dosage units. In this kit, each dosage units each consisting of a combination of progestin at a daily dosage equivalent in progestational activity to 30–150 µg levonorgestrel and an anti-estrogen at a daily dosage equivalent to 0.5–25 mg of the compound of Example 32. The daily dosage arrangements are preferably arranged in a blister pack or in a dial pack type tablet dispenser. Specific referred progestins and anti-estrogens and the specifically preferred dosages of each combination dosage unit are described above.

What is claimed is:

1. A method of providing contraception which comprises administering to a female of childbearing age a contraceptive effective amount of a combination of a non-uterotropic anti-estrogen of formulas I or II having the structure

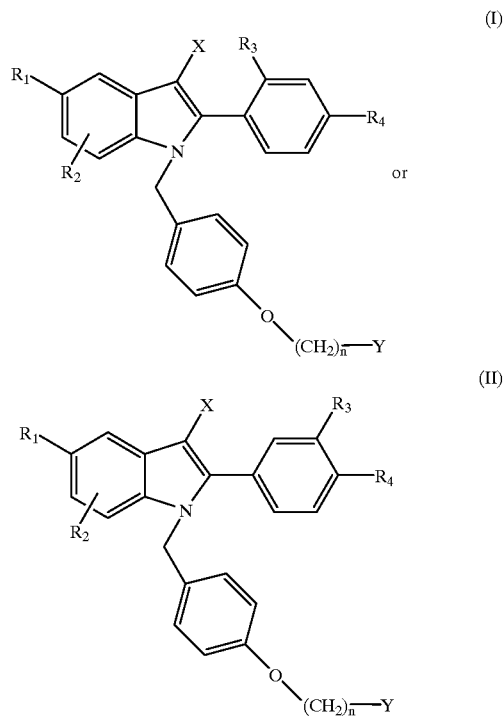

wherein:
R$_1$ is H, OH, carboalkoxy of 2–12 carbon atoms, alkoxy of 1–12 carbon atoms, halogen or mono- or polyfluoroalkoxy of 1–12 carbon atoms;
R$_2$ is H, OH, carboalkoxy of 2–12 carbon atoms, alkoxy of 1–12 carbon atoms, halogen, mono- or polyfluoroalkoxy of 1–12 carbon atoms, cyano, alkyl of 1–6 carbon atoms, or trifluoromethyl, with the proviso that, when R$_1$ is H, R$_2$ is not OH,
R$_3$ and R$_4$ are each, independently, H, OH, carboalkoxy of 2–12 carbon atoms, alkoxy of 1–12 carbon atoms, halogen, mono- or poly-fluoroalkoxy of 1–12 carbon atoms, or cyano, with the proviso that, when $R_1$ is H, $R_2$ is not OH, X is H, alkyl of 1–6 carbon atoms, cyano, nitro, triflouromethyl, or halogen;

n is 2 or 3;

Y is a saturated, partially saturated or unsaturated 5–7 membered heterocycle containing a nitrogen, which may optionally contain a second heteroatom selected from the group consisting of —O—, —NH—, alkylamine of 1–6 carbon atoms, —N═, and $S(O)_m$;

m is 0–2;

or a pharmaceutically acceptable salt thereof, and a progestin for 28 consecutive days per 28-day menstrual cycle.

2. The method according to claim 1, wherein

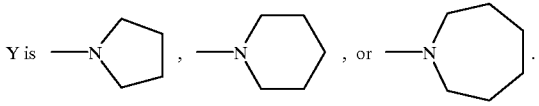

3. The method according to claim 1, wherein the progestin is selected from the group consisting of levonorgestrel, norgestrel, desogestrel, 3-ketodesogestrel, norethindrone, gestodene, norethisterone acetate, norgestimate, osaterone, cyproterone acetate, trimegestone, dienogest, and drospirenone.

4. The method according to claim 3, wherein the progestin is levonorgestrel.

5. The method according to claim 4, wherein the antiestrogen is selected from the group consisting of a) 5-benzyloxy-2-(4-ethoxy-phenyl)-3-methyl-1-[4-(2-piperidin-1-yl-ethoxy)-benzyl]-1H-indole or a pharmaceutically acceptable salt thereof;

b) 5-benzyloxy-2-phenyl-3-methyl-1-[4-(2-azepan-1-yl-ethoxy)-benzyl]-1H-indole or a pharmaceutically acceptable salt thereof;

c) 5-benzyloxy-2-(4-benzyloxy-phenyl)-3-methyl-1-[4-(2-piperidin-1-yl-ethoxy)-benzyl]-1H-indole or a pharmaceutically acceptable salt thereof;

d) 5-benzyloxy-2-(4-benzyloxy-phenyl)-3-methyl-1-[4-(2-azepan-1-yl-ethoxy)-benzyl]-1H-indole or a pharmaceutically acceptable salt thereof;

e) 5-benzyloxy-2-(4-flouro-phenyl)-3-methyl-1-[4-(2-azepan-1-yl-ethoxy)-benzyl]-1H-indole or a pharmaceutically acceptable salt thereof;

f) 5-benzyloxy-2-(4-flouro-phenyl)-3-methyl-1-[4-(2-piperidin-1-yl-ethoxy)-benzyl]-1H-indole or a pharmaceutically acceptable salt thereof;

g) 5-benzyloxy-2-(4-chloro-phenyl)-3-methyl-1-[4-(2-piperidin-1-yl-ethoxy)-benzyl]-1H-indole or a pharmaceutically acceptable salt thereof;

h) 5-benzyloxy-2-[3,4-methylenedioxy-phenyl]-3-methyl-1-[4-(2-piperidin-1-yl-ethoxy)-benzyl]-1H-indole or a pharmaceutically acceptable salt thereof;

i) 5-benzyloxy-2-[4-isopropoxy-phenyl]-3-methyl-1-[4-(2-piperidin-1-yl-ethoxy)-benzyl]-1H-indole or a pharmaceutically acceptable salt thereof;

j) 5-benzyloxy-2-[4-methyl-phenyl]-3-methyl-1-[4-(2-piperidin-1-yl-ethoxy)-benzyl]-1H-indole or a pharmaceutically acceptable salt thereof;

k) 5-benzyloxy-2-(3-benzyloxy-phenyl)-3-methyl-1-[4-(2-piperidin-1-yl-ethoxy)-benzyl]-1H-indol or a pharmaceutically acceptable salt thereof;

l) 1-[4-(2-azepan-1-yl-ethoxy)-benzyl]-5-benzyloxy-2-(3-benzyloxy-phenyl)-3-methyl-1H-indole or a pharmaceutically acceptable salt thereof;

m) 5-benzyloxy-2-(4-benzyloxy-3-fluoro-phenyl)-3-methyl-1-[4-(2-piperidin-1-yl-ethoxy)-benzyl]-1H-indole or a pharmaceutically acceptable salt thereof;

n) 5-benzyloxy-2-(4-benzyloxy-3-fluoro-phenyl)-3-methyl-1-[4-(2-azepan-1-yl-ethoxy)-benzyl]-1H-indole or a pharmaceutically acceptable salt thereof;

o) 5-benzyloxy-2-(3-methoxy-phenyl-1-[4-(2-piperidin-1-yl-ethoxy)-benzyl]-3-methyl-1H-indole or a pharmaceutically acceptable salt thereof;

p) 5-benzyloxy-3-methyl-1-[4-(2-piperidin-1-yl-ethoxy)-benzyl]-2-(4-trifluoromethoxy-phenyl-1H-indole or a pharmaceutically acceptable salt thereof;

q) 5-benzyloxy-2-(4-benzyloxy-phenyl)-3-methyl-1-{4-methylpiperazin-1-yl)-ethoxy]-benzyl}-1H-indole or a pharmaceutically acceptable salt thereof;

r) 1-[4-(2-azepan-1-yl-ethoxy)-benzyl]-5-benzyloxy-2-(3-methoxy-phenyl)-3-methyl-1H-indole or a pharmaceutically acceptable salt thereof;

s) 4-{3-methyl-1-[4-(2-piperidin-1-yl-ethoxy)-benzyl]-1H-indole} hydrochloride;

t) 4-{3-methyl-1-[4-(2-piperidin-1-yl-ethoxy)-benzyl]-1H-indol-2-yl}-phenol hydrochloride;

u) 3-methyl-2-phenyl-1-[4-(2-piperidine-1-yl-ethoxy)-benzyl]-1H-indol-5-ol hydrochloride;

v) 4-{5-methoxy-3-methyl-1-{4-[2-(piperidin-1-yl)-ethoxy]-benzyl}-1H-indol-2-yl}-phenol or a pharmaceutically acceptable salt thereof;

w) 2-(4-methoxy-phenyl)-3-methyl-1-{4-[2-(piperidin-1-yl)-ethoxy]-benzyl}-1H-indol-5-ol or a pharmaceutically acceptable salt thereof;

x) 5-methoxy-2-(4-methoxy-phenyl)-3-methyl-1-[4-(2-piperidin-1-yl-ethoxy)-benzyl]-1H-indole hydrochloride;

y) 1-[4-(2-azepan-1-yl-ethoxy)-benzyl]-5-methoxy-2-(4-methoxy-phenyl)-3-methyl-1H-indole hydrochloride;

z) 2-(4-ethoxy-phenyl)-3-methyl-1-[4-(2-piperidin-1-yl-ethoxy)-benzyl]-1H-indol-5-ol or a pharmaceutically acceptable salt thereof;

aa) 1-[4-(2-azepan-1-yl-ethoxy)-benzyl]-2-(4-ethoxy-phenyl)-3-methyl-1H-indol-5-ol or a pharmaceutically acceptable salt thereof;

ab) 4-{5-fluoro-3-methyl-1-[4-(2-piperidin-1-yl-ethoxy)-benzyl]-1H-indol-2-yl}-phenol hydrochloride;

ac) 1-[4-(2-azepan-1-yl-ethoxy)-benzyl]-3-methyl-2-phenyl-1H-indol-5-ol hydrochloride;

ad) 2-(4-hydroxy-phenyl)-3-methyl-1-[4-(2-pyrollidin-1-yl-ethoxy)-benzyl]-1H-indol-5-ol or a pharmaceutically acceptable salt thereof;

ae) 2-(4-hydroxy-phenyl)-3-methyl-1-[4-(2-piperidin-1-yl-ethoxy)-benzyl]-1H-indol-5-ol or a pharmaceutically acceptable salt thereof;

af) 1-[4-(2-azepan-1-yl-ethoxy)-benzyl]-2-(4-hydroxy-phenyl)-3-methyl-1H-indol-5-ol hydrochloride;

ag) 2-(4-fluoro-phenyl)-3-methyl-1-[4-(2-piperidine-1-yl-ethoxy)-benzyl]-1H-indol-5-ol hydrochloride;

ah) 1-[4-(2-azepan-1-yl-ethoxy)-benzyl]-2-(4-fluoro-phenyl)-3-methyl-1H-indol-5-ol or a pharmaceutically acceptable salt thereof;

ai) 2-(3-methoxy-4-hydroxy-phenyl)-3-methyl-1-[4-(2-piperidin-1-yl-ethoxy)-benzyl]-1H-indol-5-ol hydrochloride;

aj) 2-benzo[1,3]dioxol-5-yl-3-methyl-1-[4-(2-piperidin-1-yl-ethoxy)-benzyl]-1H-indol-5-ol hydrochloride;

ak) 2-(4-isopropoxy-phenyl)-3-methyl-1-[4-(2-piperidin-1-yl-ethoxy)-benzyl]-1H-indol-5-ol hydrochloride;

al) 1-[4-(2-azepan-1-yl-ethoxy)-benzyl]-2-(4-isopropoxy-phenyl)-3-methyl-1H-indol-5-ol hydrochloride;

am) 2-(4-cyclopenyloxy-phenyl)-3-methyl-1-[4-(2-piperidin-1-yl-ethoxy)-benzyl]-1H-indol-5-ol or a pharmaceutically acceptable salt thereof;

an) 2-(4-chloro-phenyl)-3-methyl-1-[4-(2-piperidin-1-yl-ethoxy)-benzyl]-1H-indol-5-ol hydrochloride;

ao) 2-(2,4-dimethoxy-phenyl)-3-methyl-1-[4-(2-piperidin-1-yl-ethoxy)-benzyl]-1H-indol-5-ol or a pharmaceutically acceptable salt thereof;

ap) 2-(3-hydroxy-phenyl)-3-methyl-1-[4-(2-piperidin-1-yl-ethoxy)-benzyl]-1H-indol-5-ol or a pharmaceutically acceptable salt thereof;

aq) 1-[4-(2-azepan-1-yl-ethoxy)-benzyl]-2-(3-hydroxy-phenyl)-3-methyl-1H-indole-5-ol or a pharmaceutically acceptable salt thereof;

ar) 2-(3-fluoro-4-hydroxy-phenyl)-3-methyl-1-[4-(2-piperidin-1-yl-ethoxy)-benzyl]-1H-indol-5-ol or a pharmaceutically acceptable salt thereof;

as) 2-(3-fluoro-4-hydroxy-phenyl)-3-methyl-1-[4-(azepan-1-yl-ethoxy)-benzyl]-1H-indol-5-ol or a pharmaceutically acceptable salt thereof;

at) 2-(3-methoxy-phenyl)-3-methyl-1-[4-(2-piperidin-1-yl-ethoxy)-benzyl]-1H-indole-5-ol or a pharmaceutically acceptable salt thereof;

au) 3-methyl-1-[4-(2-piperidin-1-yl-ethoxy)-benzyl]-2-(4-trifluoromethoxy-phenyl)-1H-indole-5-ol or a pharmaceutically acceptable salt thereof;

av) 3-chloro-2-(4-hydroxy-phenyl)-1-[4-(2-pyrrolidin-1-yl-ethoxy)-benzyl]-1H-indol-5-ol hydrochloride;

aw) 3-chloro-2-(4-hydroxy-phenyl)-1-[4-(2-piperidin-1-yl-ethoxy)-benzyl]-1H-indol-5-ol hydrochloride;

ax) 3-chloro-2-(4-hydroxy-phenyl)-1-[4-(2-azepan-1-yl-ethoxy)-benzyl]-1H-indol-5-ol hydrochloride;

ay) 3-chloro-2-(4-hydroxy-2-methyl-phenyl)-1-[4-(2-piperidin-1-yl-ethoxy)-benzyl]-1H-indol-5-ol or a pharmaceutically acceptable salt thereof;

az) 2-(4-hydroxy-phenyl)-3-ethyl-1-[4-(2-piperidin-1-yl-ethoxy)-benzyl]-1H-indol-5-ol hydrochloride;

ba) 5-hydroxy -2-(4-hydroxy-phenyl)-1-[4-(2-piperidin-1-yl-ethoxy)-benzyl]-1H-indole-3-carbonitrile hydrochloride;

bb) 1-[4-(2-azepan-1-yl-ethoxy)-benzyl]-5-hydroxy-2-(4-hydroxy-phenyl)-1H-indole-3-cabonitrile hydrochloride;

bc) di-propionate of 1-[4-(2-azepan-1-yl-ethoxy)-benzyl]-2-(4-hydroxy-phenyl)-3-methyl-1H-indol-5-ol hydrochloride;

bd) di-pivalate of 1-[4-(2-azepan-1-yl-ethoxy)-benzyl]-2-(4-hydroxy-phenyl)-3-methyl-1H-indol-5-ol hydrochloride;

be) di-pivalate ester of 2-(4-hydroxy-phenyl)-3-methyl-1-[4-(2-piperidin-1-yl-ethoxy)-benzyl]-1H-indol-5-ol or a pharmaceutically acceptable salt thereof.

6. The method according to claim 5, wherein the anti-estrogen is 1-[4-(2-azepan-1-yl-ethoxy)-benzyl]-2-(4-hydroxy-phenyl)-3-methyl-1H-indol-5-ol or a pharmaceutically acceptable salt thereof.

7. The method according to claim 6, wherein the same dosage of the anti-estrogen and progestin combination is administered in each of the 28 days.

8. The method according to claim 5, wherein the antiestrogen is 1-[4-(2-azepan-1-yl-ethoxy)-benzyl]-2-(4-hydroxy-phenyl)-3-methyl-1H-indol-5-ol acetate.

9. The method according to claim 8, wherein the same dosage of the anti-estrogen and progestin combination is administered in each of the 28 days.

10. A method of providing contraception which comprises administering to a female of child bearing age a combination of a daily dosage of 0.5–25 mg 1-[4-(2-azepan-1-yl-ethoxy)-benzyl]-2-(4-hydroxy-phenyl)-3-methyl-1H-indol-5-ol acetate and 30–150 µg levonorgestrel for 28 consecutive days per 28 day menstrual cycle.

11. The method according to claim 10, wherein the same dosage of the combination is administered in each of the 28 days.

12. A contraceptive kit adapted for daily oral administration which comprises 28 separate dosage units, each containing a combination of a non-uterotrophic anti-estrogen and a progestin, wherein the anti-estrogen is a compound of formulas I or II having the structure

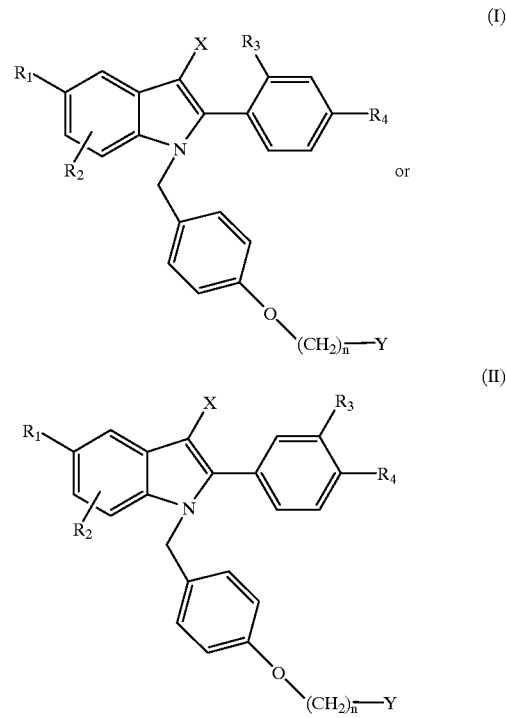

wherein:

$R_1$ is H, OH, carboalkoxy of 2–12 carbon atoms, alkoxy of 1–12 carbon atoms, halogen or mono- or poly-fluoroalkoxy of 1–12 carbon atoms;

$R_2$ is H, OH, carboalkoxy of 2–12 carbon atoms, alkoxy of 1–12 carbon atoms, halogen, mono- or poly-fluoroalkoxy of 1–12 carbon atoms, cyano, alkyl of 1–6 carbon atoms, or trifluoromethyl, with the proviso that, when $R_1$ is H, $R_2$ is not OH, $R_3$ and $R_4$ are each, independently, H, OH, carboalkoxy of 2–12 carbon atoms, alkoxy of 1–12 carbon atoms, halogen, mono- or poly-fluoroalkoxy of 1–12 carbon atoms, or cyano, with the proviso that, when $R_1$ is H, $R_2$ is not OH, X is H, alkyl of 1–6 carbon atoms, cyano, nitro, triflouromethyl, or halogen;

n is 2 or 3;

Y is a saturated, partially saturated or unsaturated 5–7 membered heterocycle containing a nitrogen, which may optionally contain a second heteroatom selected from the group consisting of —O—, —NH—, alkylamine of 1–6 carbon atoms, —N═, and $S(O)_m$;

m is 0–2;

or a pharmaceutically acceptable salt thereof, and the progestin is selected from the group consisting of levonorgestrel, norgestrel, desogestrel, 3-ketodesogestrel, norethindrone, gestodene, norethisterone acetate, norgestimate, osaterone, cyproterone acetate, trimegestone, dienogest, and drospirenone.

13. The kit according to claim 12, wherein the antiestrogen is 1-[4-(2-azepan-1-yl-ethoxy)-benzyl]-2-(4-hydroxy-phenyl)-3-methyl-1H-indol-5-ol acetate and the progestin is levonorgestrel.

* * * * *